United States Patent
Rhodes et al.

(10) Patent No.: US 7,549,317 B2
(45) Date of Patent: *Jun. 23, 2009

(54) PARTICLE-BASED FLOW SENSOR

(75) Inventors: Michael L. Rhodes, Richfield, MN (US); Brian C. Krafthefer, Stillwater, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/836,471

(22) Filed: Aug. 9, 2007

(65) Prior Publication Data

US 2007/0271903 A1    Nov. 29, 2007

Related U.S. Application Data

(63) Continuation of application No. 11/161,221, filed on Jul. 27, 2005, now Pat. No. 7,275,415, which is a continuation-in-part of application No. 10/749,498, filed on Dec. 31, 2003, now Pat. No. 6,971,258.

(51) Int. Cl.
    *G01M 15/10* (2006.01)
(52) U.S. Cl. .................. 73/23.31; 73/28.01; 73/28.02; 73/114.69; 73/114.74; 123/568.16; 123/568.21
(58) Field of Classification Search .............. 73/28.01, 73/28.02, 23.31, 114.74, 114.69; 123/568.16, 123/568.21
    See application file for complete search history.

(56) References Cited

U.S. PATENT DOCUMENTS

| 3,595,078 | A | 7/1971 | Beck et al. |
|---|---|---|---|
| 3,635,082 | A | 1/1972 | Preliwitz et al. |
| 3,739,180 | A | 6/1973 | Carlson |
| 3,762,221 | A | 10/1973 | Coulthard |
| 3,813,939 | A | 6/1974 | Head |
| 3,878,461 | A | 4/1975 | Saint-Andre |
| 3,982,126 | A | 9/1976 | Von Alfthan |
| 4,307,061 | A | 12/1981 | Sarholz |
| 4,485,794 | A | 12/1984 | Kimberley et al. |

(Continued)

FOREIGN PATENT DOCUMENTS

DE    19536705    4/1997

(Continued)

OTHER PUBLICATIONS

"BG-3 Transient & Steady-State Particulate Flow Sampling System," Sierra Instruments, Inc., 4 pages, prior to Dec. 31, 2003. Previously Provided in Parent Application 11161221.

*Primary Examiner*—Erick Solis
(74) *Attorney, Agent, or Firm*—Kris T. Fredrick

(57) ABSTRACT

A fluid conveyance apparatus having more than one particulate matter sensing probe situated at two or more locations on the apparatus. Signals from the probes from at least two locations may indicate particulate matter flowing within a fluid through the conveyance apparatus. The times between signals may be indicated the rate of movement of the particulate matter in the conveyance apparatus and also a flow rate and direction of the fluid. The sensing probe signals may be processed into control signals that may go to a flow control mechanism. An example application of the flow control mechanism may be for an exhaust gas recirculation system of an engine.

19 Claims, 6 Drawing Sheets

U.S. PATENT DOCUMENTS

| | | | |
|---|---|---|---|
| 4,514,257 A | 4/1985 | Karlsson et al. | |
| 4,529,309 A | 7/1985 | Pettersson et al. | |
| 4,812,287 A * | 3/1989 | Nakayama et al. | 420/41 |
| 4,888,948 A | 12/1989 | Fisher et al. | |
| 5,076,237 A | 12/1991 | Hatman et al. | |
| 5,180,983 A | 1/1993 | Murata et al. | |
| 5,679,907 A | 10/1997 | Ruck | |
| 5,681,986 A | 10/1997 | Merk et al. | |
| 5,864,239 A | 1/1999 | Adams et al. | |
| 5,898,257 A | 4/1999 | Sequerra et al. | |
| 6,138,504 A * | 10/2000 | Lewis et al. | 73/114.33 |
| 6,192,740 B1 | 2/2001 | Thomas et al. | |
| 6,341,501 B2 | 1/2002 | Sugimoto et al. | |
| 6,434,476 B1 * | 8/2002 | Zagone | 701/115 |
| 6,466,022 B1 | 10/2002 | Koopmans | |
| 6,489,775 B1 | 12/2002 | Rigby et al. | |
| 6,512,375 B1 | 1/2003 | Yamada et al. | |
| 6,583,539 B1 | 6/2003 | Zamora | |
| 6,634,210 B1 | 10/2003 | Bosch et al. | |
| 7,066,037 B2 | 6/2006 | Keskinen et al. | |
| 2002/0000810 A1 | 1/2002 | Bauer et al. | |
| 2003/0041845 A1 * | 3/2003 | Akao et al. | 123/568.16 |
| 2003/0234012 A1 | 12/2003 | Bosteels | |
| 2004/0031386 A1 | 2/2004 | Rauchfuss et al. | |
| 2005/0050968 A1 | 3/2005 | Trenholm | |
| 2007/0119434 A1 * | 5/2007 | Minegishi et al. | 123/568.21 |

FOREIGN PATENT DOCUMENTS

| | | |
|---|---|---|
| DE | 19853841 | 6/1999 |
| DE | 10128869 | 1/2002 |
| EP | 0353196 | 1/1990 |
| GB | 2002548 | 2/1979 |
| JP | 60123761 | 7/1958 |
| JP | 60039543 | 3/1985 |
| JP | 60100046 | 6/1985 |

* cited by examiner

PARTICLE-BASED FLOW SENSOR

BACKGROUND

The present invention is a continuation of U.S. patent application Ser. No. 11/161,221 filed Jul. 27, 2005, incorporated herein by reference, which is a continuation-in-part of U.S. patent application Ser. No. 10/749,498, filed Dec. 31, 2003, and entitled PARTICULATE MATTER SENSOR, which is incorporated herein by reference.

The invention pertains to sensors and particularly to exhaust sensors. More particularly, the invention pertains to particulate sensors.

SUMMARY

The invention has more than one particulate matter type sensor situated in series in a mechanism for a particulate matter flow measurements.

DESCRIPTION

There is an interest in directly measuring exhaust flow in an engine, e.g., a diesel engine. Such measurements may be useful for emissions control. Engine emissions may be controlled by feeding some of the exhaust back into the inlet of the engine in a process referred to as "exhaust gas recirculation" or EGR. Monitoring an amount of exhaust gas being recirculated, referred to as a "rate", may be limited by high temperatures, corrosive gases, and pressure variations that make related art sensors unsuitable for monitoring EGR rate.

The present system may be based on using two particulate matter sensors. The sensors may be arranged in series with a known gap between them. Flow may be indicated by a time lag between the sensor responses, i.e., phase difference. The present system may be capable of operating at very high temperatures (i.e., greater than 800 degrees C.). The system is insensitive to pressure variations and chemical composition of the exhaust gases.

Figure 1:
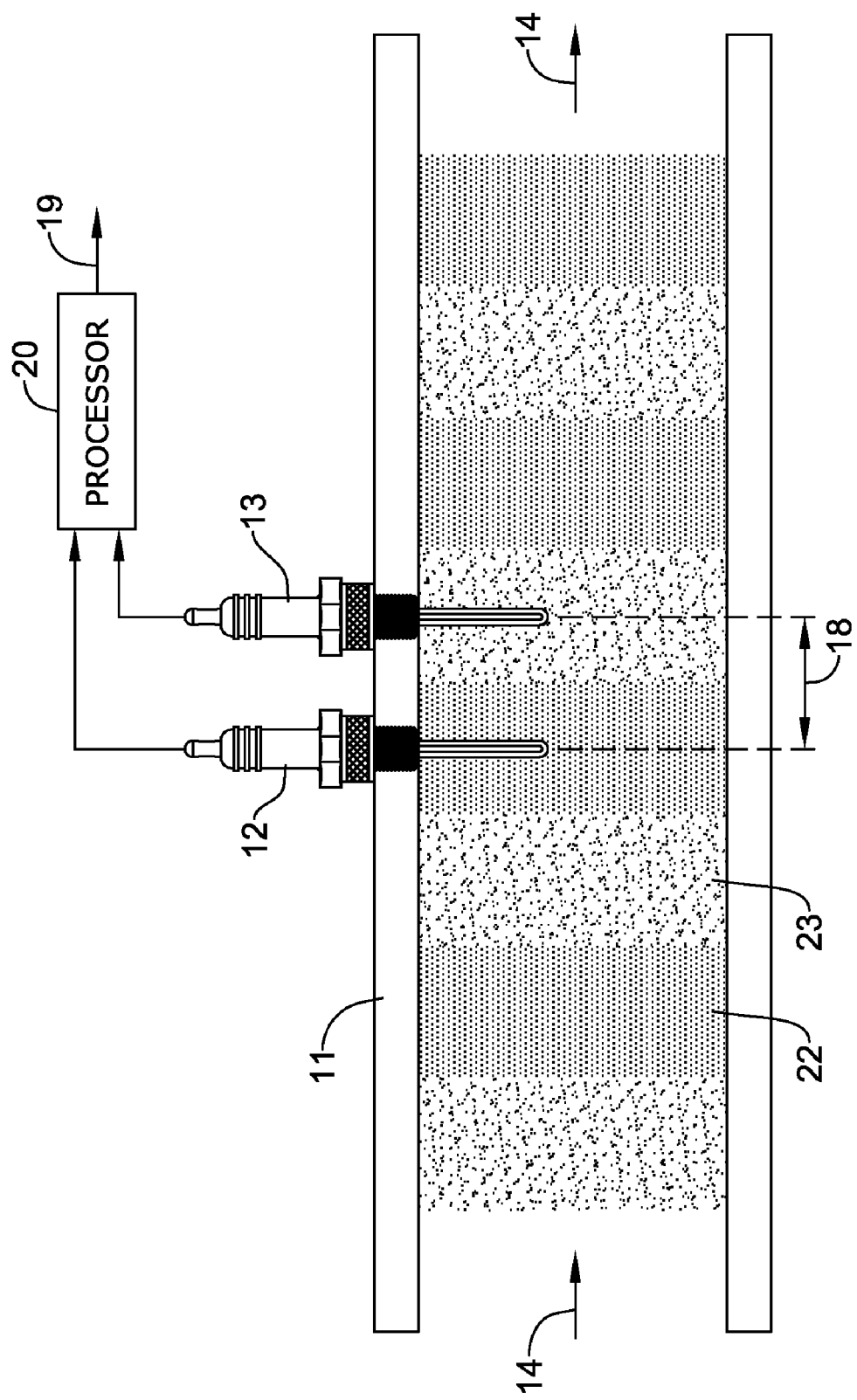
FIG. 1 is a cutaway view of an exhaust pipe showing two particulate sensors at a distance from each other in the direction of the fluid.

In FIG. 1, an exhaust mechanism 11 for having a flow of a gas in an exhaust system of an engine may have several soot or particulate matter (PM) sensors 12 and 13 situated in series along a line being in the same direction of the exhaust gas flow. Each of sensors 12 and 13 may respond quantitatively to particulates in the same way. The exhaust flow 14 may have a variation of particulate matter or particle charge in the engine exhaust. The variations of particle charge may occur in a cyclic fashion in the gas flow 14.

Figure 2:
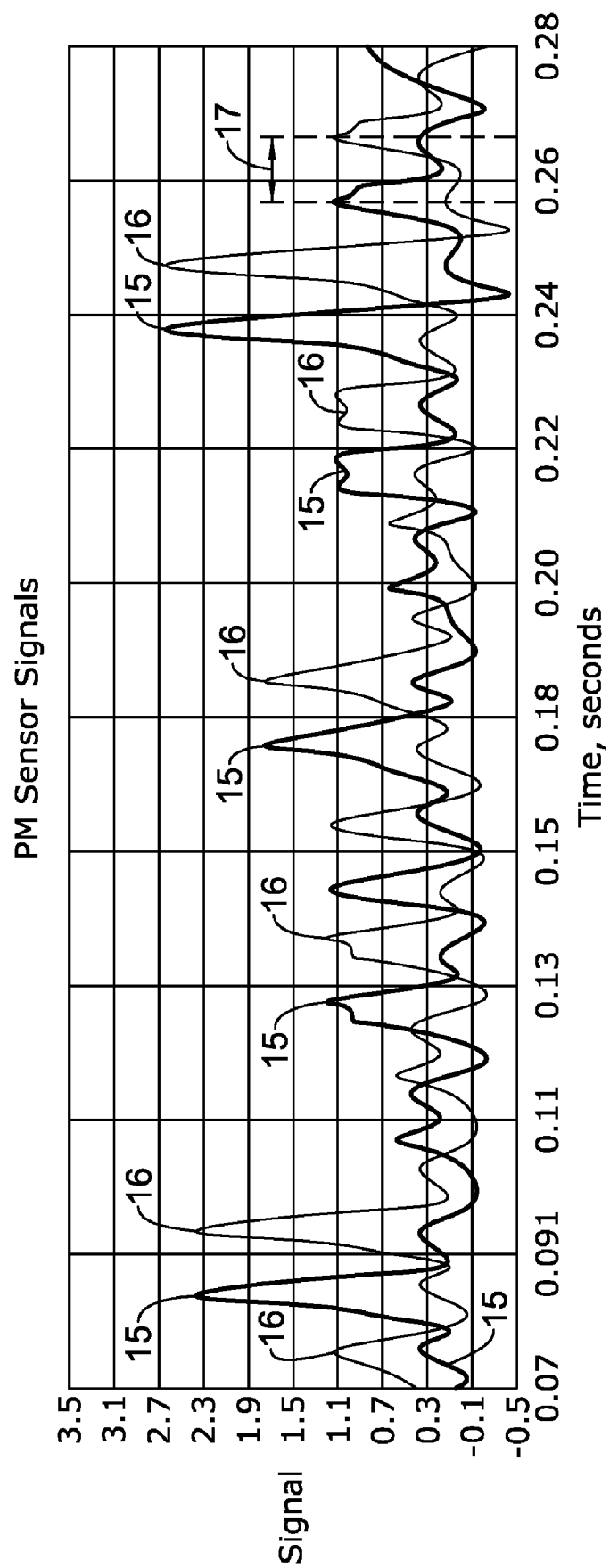
FIG. 2 shows a charge from two particulate matter sensors in a flowing exhaust stream of an engine.

Signals 15 and 16 from the up-stream sensor 12 and the down-stream sensor 13 are shown in a graph of FIG. 2. The graph shows the magnitude of the signal which represents a density of the particulate matter, as sensed by sensor 12 and sensor 13, versus time. The high magnitude portions of signals 15 and 16 represent the sensing of the greater density of PM (i.e., particle charge), as shown by portions 22 in FIG. 1. The low magnitude portions of signals 15 and 16 represent the lower density PM as shown by portions 23. The gradation of the PM density between portions 22 and 23 may be less distinct than as shown in FIG. 1. FIG. 1 merely reveals an illustrative example, as there may be other density patterns of the PM in the exhaust gas flow 14. A difference of time between the pulse detected by the sensor 12 and the pulse detected by sensor 13 may indicated the velocity of the exhaust flow 14. The dimension 17 indicates the time differences ΔT between the sensing of the pulse or denser portion of PM in the exhaust flow by the sensor 12 and sensor 16, respectively. Dimension 17 is about 0.01 second in FIG. 2. The distance 18 between sensor 12 and sensor 13 may be L centimeters (cm). The measured dimensions L/ΔT=exhaust flow rate. In the present example, L/ΔT may be L cm/0.01 sec=100 L cm/sec.

The outputs of PM sensors 15 and 16 may go to a processor 20 which indicates at its output 19 a flow rate of the particulate matter. This flow rate of the particulate matter may be assumed to be the rate of the exhaust gas 14 flow.

Sensors 12 and 13 may be close enough in distance 18 so that each cycle is longer than distance 18, even at high rpm of the engine. Sensors, like 12 and 13, may be situated proximate to one or more cylinders for possibly clearer signals from the sensors of the particulate matter density; however, the sensors may be situated further away from the cylinder or cylinders in the manifold or the exhaust pipe. Various designs may be incorporated in accordance with the desired application and use of exhaust flow information.

Figure 3C:
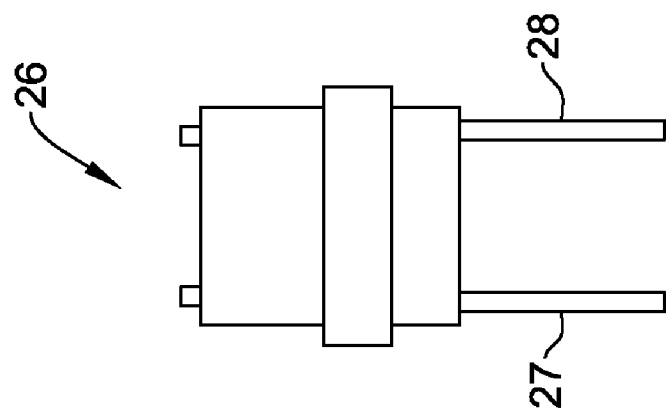
FIGS. 3a, 3b and 3c show several styles of a dual electrode particulate matter sensor.
Figure 3B:
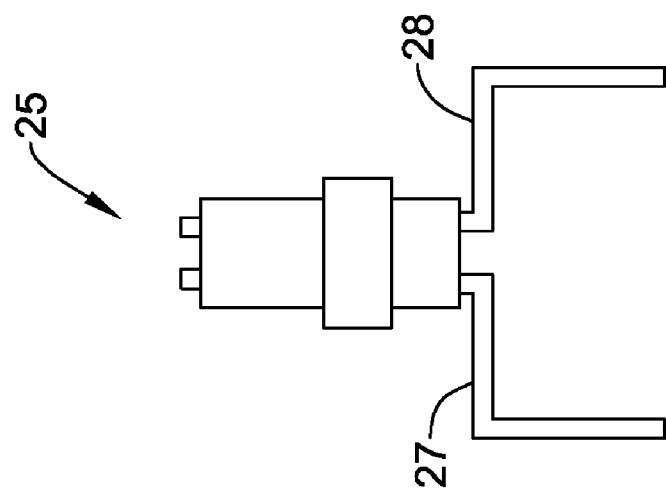
Figure 3A:
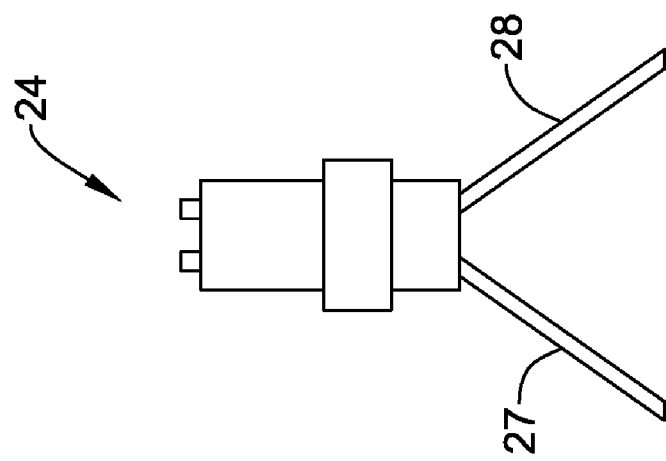

Sensors 12 and 13 may be combined into one housing to effectively result in a two probe sensor 24, 25 or 26 as shown in FIGS. 3a, 3b and 3c, respectively. Sensor 24 may have electrodes 27 and 28 turned or bendable so that the sensor may be inserted into the fitting of the manifold or exhaust pipe during installation or replacement. The same approach may be used for sensor 25. The configuration of sensor 26 permits installation of replacement without temporarily affecting the probes or electrodes 27 and 28.

The flow control mechanism 32 for the EGR may be controlled according to the flow of the particulate matter of exhaust gas 14 as sensed by particulate matter sensors 12 and 13 situated in conveyance or tube 55 from the exhaust pipe 48 to flow control mechanism or EGR valve 32 as described in the present specification. The sensors 12 and 13 may be substituted with a sensor 24, 25 or 26, as shown in FIGS. 3a, 3b and 3c, respectively, or a sensor of another configuration. There may be another set of PM sensing probes of sensor 24 situated in exhaust pipe 48 downstream from the connection to the tube or pipe 55. Sensor 24 may also send flow rate information to processor 20, as well as sensors 12 and 13. However, one set of PM sensor probes may be sufficient for EGR control based on exhaust gas 14 flow as indicated by the PM flow rate.

The sensed PM charge signals from sensors 12 and 13 may go to processor 20. Processor 20 may provide a flow signal on output 19 to the controller 60 which may process the flow signal information, possibly along with other parameter information, to provide a control signal via connection 73 to the valve or flow control mechanism 32 for controlling the flow of recirculated exhaust gas 14 may be combined with incoming air 36 into a mixture 56 before the intake manifold 35 at location 38 or within the intake manifold 35. Then the mixture of air 36 and exhaust gas 14 may enter the intake ports before or after fuel is added to the mixture. Controller 60 may utilize, besides recirculated exhaust gas 14 flow information 19 based on the PM flow, from processor 20, information from engine sensors via a connection 72, crank angle or speed information from flywheel position sensor 59 and/or exhaust gas 14 pressure information from sensors 57 and 58 in the EGR tube 55, and possibly other information, for determining an amount of control of the flow control mechanism or valve 32 upon the flow of recirculated gas 14, as indicated by processor 20, to the engine's intake system. The flow of exhaust gas 14 may be controlled according to the amount of the sensed and inferred flow, without significant dependence on the other inputs to controller 60. The flow sensors 12 and 13 may provide a feedback signal to controller 60 directly or via processor 20, to maintain a prescribed or variable EGR flow, as desired.

Figure 4:
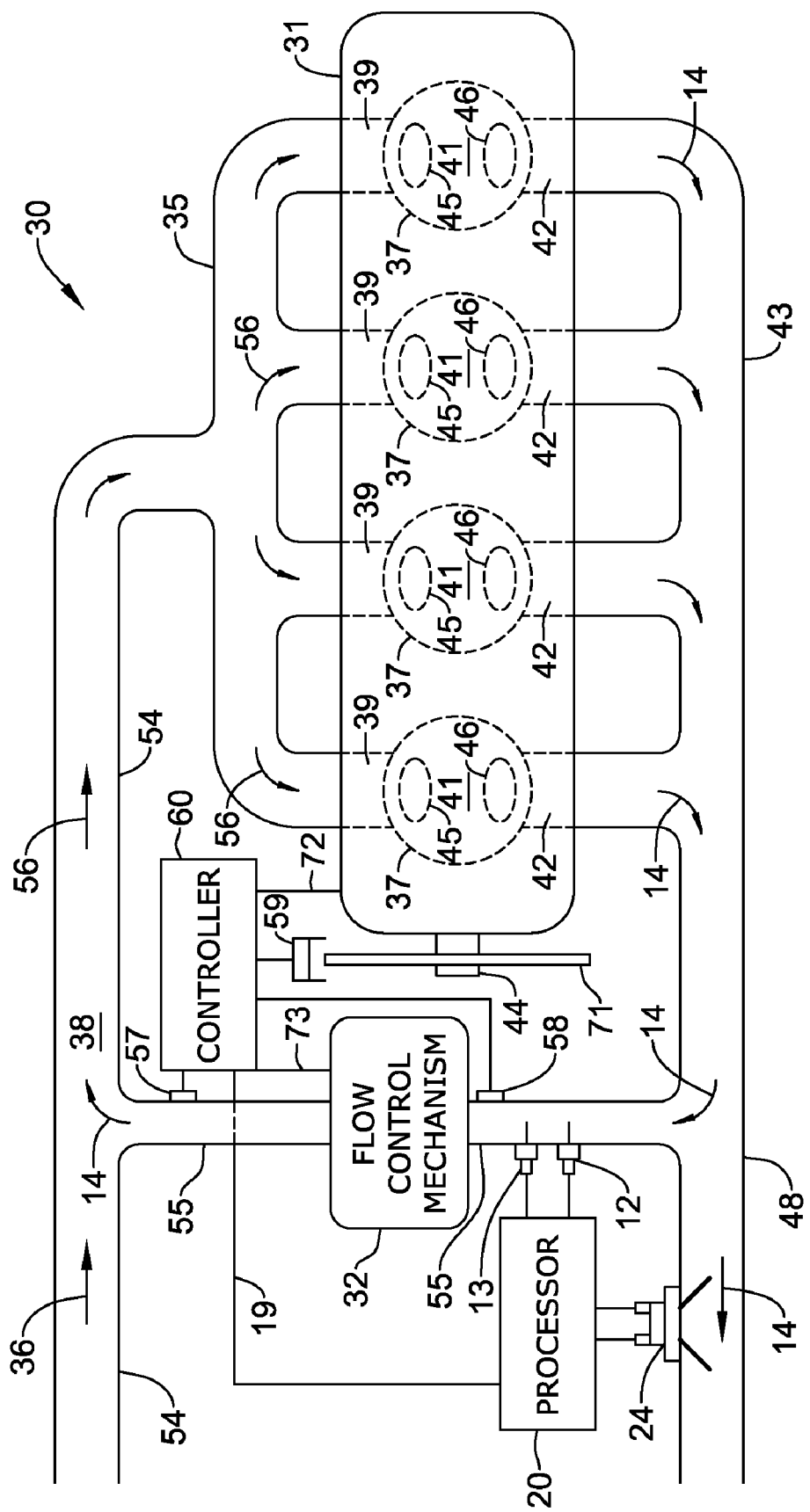
FIG. 4 reveals a particulate matter flow sensor utilized in conjunction with an exhaust gas recirculation system of an engine.

FIG. 4 shows a system 30 having an engine 31 and an exhaust gas recirculation (EGR) mechanism having a valve 32. Modern engines use exhaust gas recirculation (EGR) to lower the engine-out emissions of NOx emission to meet stringent emissions regulations. A turbocharger or a supercharger (not shown) may be coupled to an intake manifold 35. If there is a supercharger, charger or compressor, it may be driven by the engine 31 via a belt or other power transferring mechanism. The supercharger may a roots-type or other kind of a charger. EGR is the recirculation of some of the engine 31 exhaust gases 14 back to the engine. The exhaust gas 14 may be combined with fresh air 36 into a mixture 56 before the intake manifold 35 at location 38 or within the intake manifold 35. Then the mixture 56 of fresh air 36 and exhaust gas 14 may enter cylinders 37 via the intake ports 39 at the proper times. At this time, a certain amount of fuel may be added to the mixture 56 (via a carburetor or fuel injectors) before entering or after going through the intake valve to the cylinder. This new mixture 56 may enter the respective cylinder during an intake cycle as permitted by an intake valve 45 to cylinder 37. Subsequently, the intake valve may close and a piston 41 in the cylinder compress the mixture 56 up against a head structure (head), not explicitly shown, that is attached to the top of the block containing the cylinder. The head may cap off and seal the cylinder 37 encompassing a volume between the piston and the head. As the piston moves towards its closest position to the head (i.e., top dead center—TDC) the volume of the mixture 56 may decrease and the pressure increase dramatically while the intake valve 45 and an exhaust valve 46 situated in the head are closed thereby maintaining the seal of the volume of the mixture 56. Also, manifolds 35 and 43 may be attached to the head having ports 39 and 42 connecting the manifolds to their respective valves 45 and 46. The valves 45 and 46 may be round but appear oval in the Figure because of their slanted orientation in the head relative to the top of piston 41. Alternatively, valves 45 and 46 may be situated in the top of the cylinder block of the engine along with the respective intake and exhaust manifolds being attached to the block. The intake valve 45 and exhaust valve 46 may be opened and closed by a camshaft (not shown) that is connected to a crankshaft 44. Other mechanisms may be utilized for bringing fuel mixtures to the engine and removing exhaust gases from the engine. At about the piston's closest point to the head, the compressed mixture 56 may ignite (due to the heat of a highly compressed mixture in a diesel engine or the spark of a plug in a gasoline engine) and expand thereby providing much pressure on the piston and pushing the piston away from the head. The piston 41 may be connected to the crankshaft 44 that is rotated by the force of the burning mixture 56 upon the piston, resulting in a power cycle. As the piston approaches its farthest position from the head (i.e., bottom dead center—BDC), the exhaust valve 46 may open and the piston 41 return back up the cylinder 37 and push a burnt mixture or exhaust gas 14 out of the cylinder 37 through the exhaust valve 46 into an exhaust manifold 43 via an exhaust port 42, resulting in an exhaust cycle. The exhaust valve 46 may close and the intake valve open thereby permitting the piston 41 to draw in another mixture 56 including some fuel, into the cylinder 37 during its next intake cycle as the piston 41 moves down cylinder 37 away from the head. The sequence or intake, compression, power and exhaust cycles may repeat themselves for a given piston 41 and cylinder 37 over the next two rotations of the crankshaft 44. Each of the other pistons 41 and cylinders 37 may proceed through the same process. However, each piston may have its sequence of cycles offset from the other pistons somewhere from one-half to one-and-one-half revolutions of the crankshaft 44. Thus, in the case of the four cylinder engine 31 shown in FIG. 4, there may be one power cycle from one of the pistons 41 during each half revolution of the crankshaft 44. Engine 31 may instead have a different number of cylinders and configuration such an in-line, "V" or opposed cylinder arrangement. The engine may be an internal combustion engine of another kind not having pistons. An example of such engine may be a Wankel engine.

The power of the engine 31 may be increased by compressing the mixture 56, along with the fuel, before it enters the cylinder 37, with a mechanism such as a turbocharger. The exhaust gases 14 exiting the engine 31 into manifold 43 may go via an exhaust pipe 48 and turn the turbocharger, or exit the engine via pipe 48. Fresh air 36 may be drawn in via an intake tube 54 that is connected to the manifold 35.

EGR may be accomplished by means of a pipe 55, or other device for conveyance, which may connect the exhaust manifold 43 or exhaust pipe 48 to the intake manifold or air intake tube 54. In the EGR flow pipe 55, an on/off valve or a proportional flow valve may be situated in the pipe as the valve 32. When the on/off valve or the proportional flow valve is used, either one may be controlled at a conventional, slow time scale to modulate EGR as a function of load and speed of the crankshaft 44 of engine 31. In both these cases, the exhaust pressure should be greater than the intake pressure to provide an EGR flow in the right direction. The intake pressure and the exhaust pressure may be measured by pressure sensors 57 and 58, respectively. Sensors 57 and 58 may be connected to a controller 60. Signals from the sensors 57 and 58 may be utilized to determine the differential pressure across the flow control mechanism 32. This pressure may also be detected by a differential or delta pressure sensor appropriately situated. The speed or revolution rate, count or angle of the crankshaft may be detected by a speed or position sensor 59 that is proximate to a flywheel 71 which is attached to crankshaft 44. Sensor 59 may be connected to controller 60. The valve or flow control mechanism 32 may be connected to controller 60 via connection 73. There may be various parameter sensor signals from engine 31 provided to controller 60 via a connection 72. Controller 60 may utilize mathematical models and appropriate control logic, look-up tables, or other schemes, in computing control signals from engine-related parameters for the flow control mechanism 32.

The smoke emitted from an engine 31 (e.g., a diesel) is normally charged by the weak plasma generated in the combustion process. The charged particulates (PM) 72 emitted from the cylinder 37 during the exhaust cycle stream may pass conductive probes 12 and 13 connected to a charge amplifier 61 which records the concentration of particles as a function of time (i.e., time-domain). A signal representing this concentration may then be digitized and passed to a microprocessor for analysis.

Figure 5:
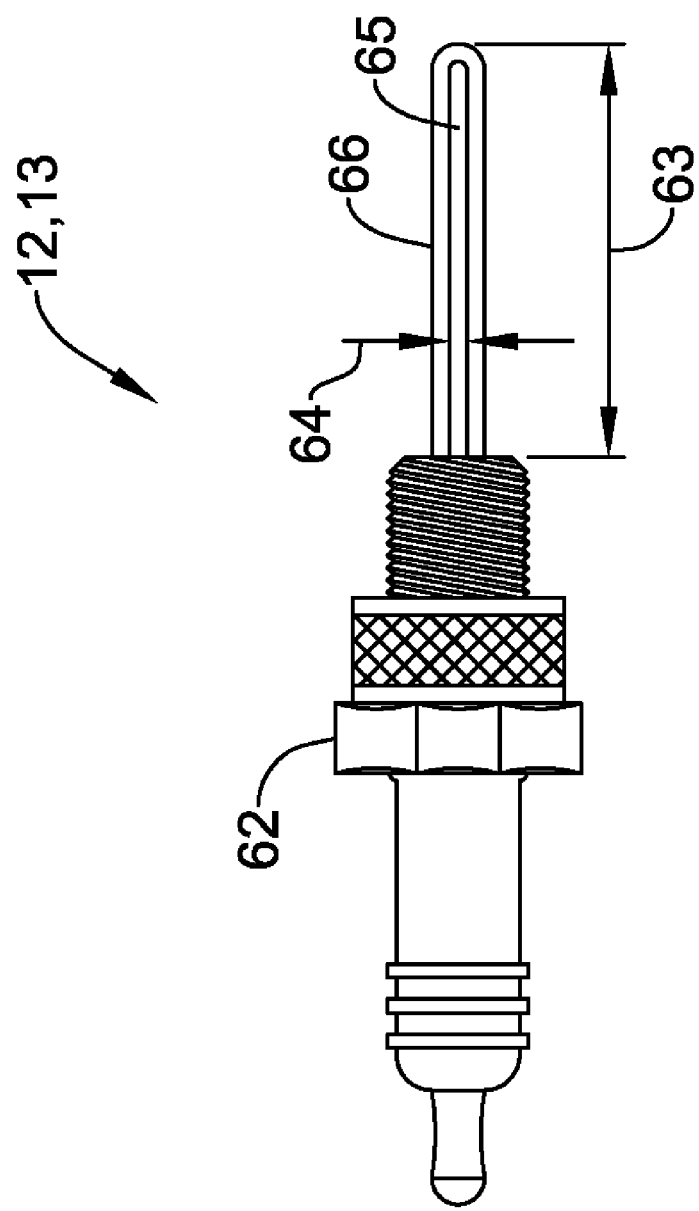
FIG. 5 shows an individual particulate matter sensor.

The PM transducer probes 12 and 13 may each have a spark-plug-like support 62 as shown in FIG. 5. The PM probe may provide an output based on the PM formed on the probe. The probe may be placed in a path of the exhaust 14 of the engine 31. The length 63 and diameter 64 of a probe electrode 65 may vary depending on the parameters of the sensing electronics and the engine. The probe electrode 65 may be passivated with a very thin conductive coating or layer 66 on it. This coating or layer 66 may prevent electrical shorting by the soot layer accumulated by the probe during the operation of engine 31. The passivation material 66 may be composed of SiN4, cerium or other oxide, and/or the like. The thickness of the passivation layer 66 on the probe electrode 65 may be between 0.001 and 0.020 inch. A nominal thickness may be about 0.01 inch. The passivation layer 66 may be achieved with the probe electrode 65 exposed to high exhaust temperatures or may be coated with a layer via a material added to the engine's fuel.

Sensor or probe 12, 13 may have various dimensions. Examples of an electrode 65 length dimension 63 may be between 0.25 and 12 inches. A nominal value of the length 63 may be about 3 to 4 inches. Examples of a thickness or diameter dimension 64 may be between 1/32 inch and 3/8 inch. A nominal thickness may be about 1/8 inch.

An example of the probe may include a standard spark plug housing 62 that has the outside or ground electrode removed and has a 4 to 6 inch metal extension of about 1/8 inch thickness or diameter welded to a center electrode. The sensor 12, 13 may be mounted in the exhaust stream 14 near the exhaust manifold 43 or after a turbocharger, if there is one, of the engine 31. The sensing electrode 65 may be connected to an analog charge amplifier 61 of a processing electronics 20. The charge transients 67 from the electrode 65 of probe 12, 13 may be directly proportional to the soot (particulate) concentration in the exhaust stream 14. The extended electrode 65 may be passivated with a very thin non-conducting layer 66 on the surface of the electrode 65 exposed to the exhaust gas 14 of the engine 31. For an illustrative example, a 304 type stainless steel may grow the passivating layer 66 on the probe electrode 65 spontaneously after a few minutes of operation in the exhaust stream 14 at temperatures greater than 400 degrees C. (750 degrees F.). However, a passivating layer 66 of cerium oxide may instead be grown on the probe electrode 65 situated in the exhaust 14, by adding an organometallic cerium compound (about 100 PPM) to the fuel for the engine 31.

Other approaches of passivating the probe or electrode 65 with a layer 66 may include sputter depositing refractory ceramic materials or growing oxide layers in controlled environments. Again, the purpose of growing or depositing the passivating layer 66 on electrode 65 situated in the exhaust 14 is to prevent shorts between the electrode and the base of the spark-plug like holder 62 due to PM buildups, so that sensor or probe 12, 13 may retain its image charge monitoring activity of the exhaust stream 14. If the electrode 65 did not have the passivating layer 66 on it, probe 12, 13 may fail after a brief operating period because of an electrical shorting of the electrode 65 to the support base 62 of the sensor due to a build-up of soot or PM on the electrode.

Figure 6:
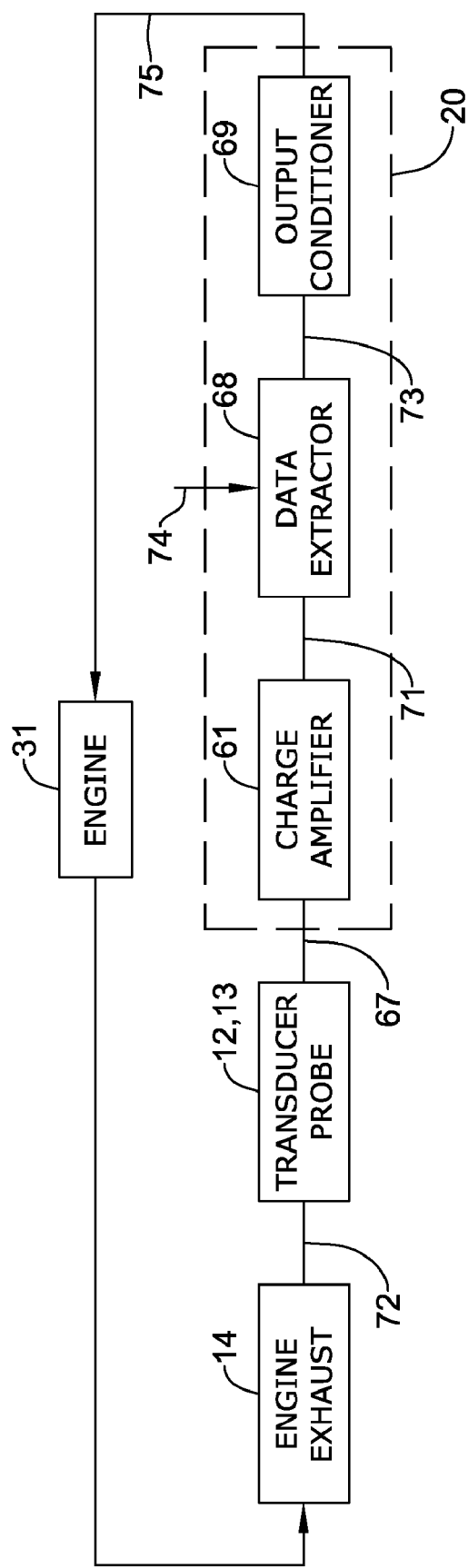
FIG. 6 is a block diagram of an illustrative example of particulate matter sensor electronics.

Processing electronics 20 may include charge amplifier 61, a data extractor 68 and an output conditioner 69. Charge amplifier 61 of FIG. 6 may be designed and situated in terms of gain, frequency response, and location. The output 71 may be a real-time signal indicating the amount of PM 72 in the exhaust 14. Signal 71 may go to a data extractor unit 68. An engine 31 crankshaft angle signal may be entered at input 74 of unit 68 for associating the specific amounts of PM at particular crankshaft angles for engine 31 analysis. An output 73 may provide an average PM 72 concentration of exhaust 14. Also, PM concentrations on a cylinder-by-cylinder basis may be revealed at output 73. Output 73 may go to an output conditioner unit 69, which may provide an engine control or diagnostic and/or engine control voltage signal 75 which may go to engine 31.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A particulate-based flow sensing system comprising:
a first particulate matter sensor; and
a second particulate matter sensor; and
wherein the first and second sensors include probe electrodes made of 304 type stainless steel, and are positioned at a distance along a path between the first and second sensors, wherein the first and second sensors each have a passivation layer on the electrodes.

2. The system of claim 1, further comprising a processor connected to the first and second sensors, wherein the processor may receive first and second signals from first and second sensors, respectively.

3. The system of claim 2, wherein:
the processor measures a time between the first and second signals; and
the processor divides the distance along the line between the first and second sensors by the time to obtain a rate of movement of the particulate matter.

4. The system of claim 3, wherein:
the particulate matter is in an exhaust gas; and
the rate of movement of the particulate matter is an indication of exhaust gas flow rate.

5. The system of claim 3, wherein processor outputs a flow rate of an exhaust gas containing the particulate matter.

6. The system of claim 2 wherein the signals from the first and second particulate matter sensors indicate a direction of flow of particulate matter through the flow control mechanism.

7. A particulate-based flow system comprising:
a flow control mechanism having an input for connection to an engine exhaust system and an output for connection to an engine intake system;
a first particulate matter sensor situated at a first location at the input of the flow control mechanism; and
a second particulate matter sensor situated at a second location at the input of the flow control mechanism;
a processor connected to the flow control mechanism, the first particulate matter sensor and the second particulate matter sensor, the processor receiving signals from the first and second particulate matter sensors;
wherein the signals from the first and second particulate matter sensors indicate a direction of flow of particulate matter through the flow control mechanism.

8. The system of claim 7, wherein the first and second particulate sensors measure a flow rate of particulate matter.

9. The system of claim 8, wherein the processor adjusts the flow control mechanism in part according to the signals from the first and second particulate matter sensors.

10. The system of claim 7, wherein the first and second sensors include probe electrodes made of 304 type stainless steel.

11. The system of claim 7, wherein:
if the flow of particulate matter is sensed to be from the input to the output of the flow control mechanism, then the flow control mechanism may allow the flow to continue; and
if the flow of particulate matter is sensed to be from the output to the input of the flow control mechanism, then the flow control mechanism may stop the flow.

12. The system of claim 11, wherein the flow control mechanism is an exhaust gas recirculation valve.

13. A method for measuring a flow, comprising:
placing a first particulate matter sensor at a first location in a conveyance mechanism for movement of a fluid containing particulate matter;
placing a second particulate matter sensor at a second location in the conveyance mechanism; and
receiving first and second signals from the first and second particulate matter sensors, respectively, which indicate a flow of a fluid containing particulate matter;
wherein the conveyance mechanism for movement of a fluid containing particulate matter includes a flow control mechanism having an input and an output and the signals from the first and second particulate matter sensors indicate a direction of flow of particulate matter through the flow control sensor.

14. The method of claim 13, further comprising:
measuring a time difference between the first and second signals and a length between the first and second locations; and
calculating the speed of the particulate matter between the first and second locations.

15. The method of claim 14, further comprising determining a flow rate of the fluid in the conveyance mechanism from the speed of the particulate matter.

16. The method of claim 15, wherein the fluid is an exhaust gas of an engine.

17. The method of claim 16, further comprising controlling an exhaust gas recirculation flow control mechanism in part according to the flow rate of the exhaust gas.

18. The method of claim 13, wherein the first and second sensors include probe electrodes made of 304 type stainless steel.

19. The method of claim 13,
wherein if the flow of particulate matter is sensed to be from the input to the output of the flow control mechanism, then the flow control mechanism may allow the flow to continue; and
if the flow of particulate matter is sensed to be from the output to the input of the flow control mechanism, then the flow control mechanism may stop the flow.

* * * * *